United States Patent

Dürr et al.

[11] Patent Number: 5,908,298
[45] Date of Patent: Jun. 1, 1999

[54] ENOSSAL SINGLE TOOTH IMPLANT WITH SPACER SLEEVE

[76] Inventors: Walter Dürr, Panoramastrasse 5, D-75196, Remchingen; Axel Kirsch, Sonnenbergstrasse 37, D-70184, Stuttgart, both of Germany

[21] Appl. No.: 08/913,504
[22] PCT Filed: Jan. 23, 1996
[86] PCT No.: PCT/DE96/00108
 § 371 Date: Sep. 16, 1997
 § 102(e) Date: Sep. 16, 1997
[87] PCT Pub. No.: WO96/29021
 PCT Pub. Date: Sep. 26, 1996

[30] Foreign Application Priority Data

Mar. 17, 1995 [DE] Germany .............. 195 09 762

[51] Int. Cl.[6] ............................................. A61C 8/00
[52] U.S. Cl. ............................................. 433/173
[58] Field of Search .................. 433/173, 174, 433/175, 176

[56] References Cited

U.S. PATENT DOCUMENTS

| 5,026,280 | 6/1991 | Dürr et al. . |
| 5,026,285 | 6/1991 | Dürr et al. . |
| 5,069,622 | 12/1991 | Rangert et al. ................. 433/173 |
| 5,125,840 | 6/1992 | Dürr et al. . |
| 5,195,891 | 3/1993 | Sulc . |
| 5,350,301 | 9/1994 | De Buck . |
| 5,417,568 | 5/1995 | Giglio . |
| 5,417,569 | 5/1995 | Perisse ................................ 433/174 |
| 5,527,182 | 6/1996 | Willoughby ....................... 433/173 |

Primary Examiner—Ralph A. Lewis
Attorney, Agent, or Firm—Hill & Simpson

[57] ABSTRACT

An enossal single tooth implant for a fixed dental prosthesis includes an essentially cylindrical base member which is insertable into a bore introduced into a jaw bone and which has a blind bore open toward one coronal end to form a face edge, a spacer sleeve attached in an anti-twist fashion to the face edge of the member, an implant post directly or indirectly introduced into the blind bore of the base member and at least partially penetrating the spacer sleeve. The spacer sleeve has a circumferential surface which forms part of a fastening head for the dental prosthesis and has an annular joining shoulder for engaging an edge of the prosthesis that has a peripherally varying spacing from the face edge of the base member to allow for adaptation to the anatomical conditions.

15 Claims, 3 Drawing Sheets

ENOSSAL SINGLE TOOTH IMPLANT WITH SPACER SLEEVE

BACKGROUND OF THE INVENTION

The invention is directed to an enossal single tooth implant for a fixed dental prosthesis, comprising an essentially cylindrical base member insertable into a bore introduced into a jaw bone, said base member comprising a blind bore open toward its coronal end, which faces away from the bone and toward the dental prosthesis, a spacer sleeve attached in anti-twist fashion to the coronal face edge of the base member, an implant post directly or indirectly introducible into the blind bore of the base member and at least partially penetrating the spacer sleeve, and a fastening head for the dental prosthesis.

Enossal implants of this type, as disclosed, for example, in German Letters Patent 40 28 855, have definitely proven themselves in practice. Since this type of implant has no adequate means for attaching a dental prosthesis in the form of a crown, which is adapted to the anatomy of the respective patient, there are occasions when this implant is considered inadequate.

U.S. Pat. No. 5,417,568 discloses a seating device for the crown structure of an implant that exhibits a curved contour, so that a favorable matching to the natural shaping of the gums can ensue. The above-described problem can be corrected by this structure.

SUMMARY OF THE INVENTION

The invention is based on the object of improving the enossal single tooth implant of German Letters Patent 40 28 855 to the effect that a dental prosthesis, particularly in the form of a crown, can be attached and can be, particularly adapted to the anatomy of the respective patient in terms of a circumferential edge of the crown.

This object is inventively achieved in that the circumference of the spacer sleeve comprises an all around joining shoulder for the dental prosthesis with the circumferential path of the shoulder deviating from the essentially cylindrical symmetry that is present in the implant, so that the shoulder has a peripherally varying spacing from the face edge of the base member for adaptation to the anatomical conditions.

The invention also proposes that the joining shoulder comprises at least one coronally directed adjustment means which may be a notch, a nose or a combination of a notch and a nose.

It can thereby be provided that the peripheral arrangement of the adjustment means is defined in terms of a circumferential angle with respect to the spacer sleeve.

The invention also provides that the dental prosthesis comprises an elevation or, respectively, depression complementary to the notch and/or nose of the adjustment means.

It can also be provided that the axial height of the joining shoulder is matched to the anatomical conditions.

The invention further proposes that the radial base height of the joining shoulder is adapted to the anatomical conditions.

It can thereby also be provided that the spacer sleeve, namely the region facing the dental prosthesis or coronal region, at least partially serves as fastening head for the dental prosthesis.

The invention also provides that the implant post is connectable to the base member and is secured against twisting.

It can be provided that the implant post, namely the coronal or upper region thereof, at least partially serves as the fastening head for the dental prosthesis.

The invention proposes that the spacer sleeve is fashioned closed at a cervical end, which faces toward the bone receiving the base member, and is insertable into the open, coronal end of the base member and comprises a bore open toward its coronal end with an inside thread for screwing or cementing the implant post in.

It can also be provided according to the invention that the spacer sleeve comprises a cervical centering collar corresponding to the face edge of the base member.

The invention also provides that the coronal end of the base member comprises a cylindrical ring recess for the acceptance of the cervical centering collar of the spacer sleeve.

It can thereby also be provided that the spacer sleeve is provided with a shoulder emplaceable onto the upper face edge of the base member.

The invention proposes that the spacer sleeve comprises a lower spacer sleeve part cementable or screwable into the base member and has an open coronal in which the implant post can be cemented or screwed, and comprises an upper spacer sleeve part provided with the centering collar comprises an upper spacer sleeve part provided with the centering collar and the shoulder for placement onto the coronal face edge of the base member.

It can also be provided that the coronal or outer region of the upper spacer sleeve part comprises a longitudinal section with a larger outside diameter than in the cervical or inner region whose outside diameter corresponds to the inside diameter of the cylindrical ring recess of the base member, whereby the shoulder is formed in the transition of the two regions of different width. The outer or coronal region of the lower spacer sleeve part comprises a head section that embraces an annular shoulder, whose outside diameter corresponds to the outside diameter in the coronal region of the upper spacer sleeve part, and the head section merges into a cervical or inner region whose outside diameter corresponds to the diameter of the inside bore of the base member.

The invention provides that the connecting means for the anti-twist fastening of the spacer sleeve on the base member is formed by the cylindrical ring recess of the base member with at least one base member positive lock element and the centering collar of the upper spacer sleeve part with a spacer sleeve positive lock element complementary to each of the base member positive lock elements.

It can thereby also be provided that the base member positive lock element(s) comprises/comprise at least one axial base member positive lock pocket and/or at least one axial base member positive lock tongue in the seating shoulder of the ring recess, and the spacer sleeve positive lock element(s) correspondingly comprises/comprise at least one complementary spacer sleeve positive lock tongue and/or at least one complementary spacer sleeve positive lock pocket.

It can also be provided that respectively six positive lock elements arranged with uniform circumferential spacing are provided at the base member and at the spacer sleeve.

The invention also provides that the lower spacer sleeve part comprises a shoulder for a tool at its coronal end.

Finally, the invention provides that the dental prosthesis is firmly joined, particularly cast, to the implant post before the insertion thereof into the spacer sleeve.

The invention is based on the surprising perception that an embodiment of the spacer sleeve with a joining shoulder having a peripherally varying spacing from the face edge of the base member guarantees that a dental prosthesis is lent a better hold at an implant post and the shaping and arrangement of the dental prosthesis can be matched better to the anatomical conditions of the jaw and tooth structure of a patient. It can thereby be provided that the spacer sleeve itself entirely or partially forms the fastening head for the dental prosthesis, whereby, in this case, the dental prosthesis is especially advantageously connected in anti-twist fashion to the spacer sleeve with corresponding elevations or, respectively, depressions at the joining shoulder of the spacer sleeve, on the one hand, and at the dental prosthesis or, respectively, a supporting framework thereof, on the other hand, whereas, second, it can also be provided that the implant post projects coronally beyond the spacer sleeve and is provided with the fastening head that, in this case, can preferably be cast with the dental prosthesis or, respectively, the supporting framework thereof.

Further features and advantages of the invention derive from the claims and from the following specification, in which an exemplary embodiment is explained in detail on the basis of the schematic drawings.

DESCRIPTION OF THE PREFERRED EMBODIMENT

Figure 1:
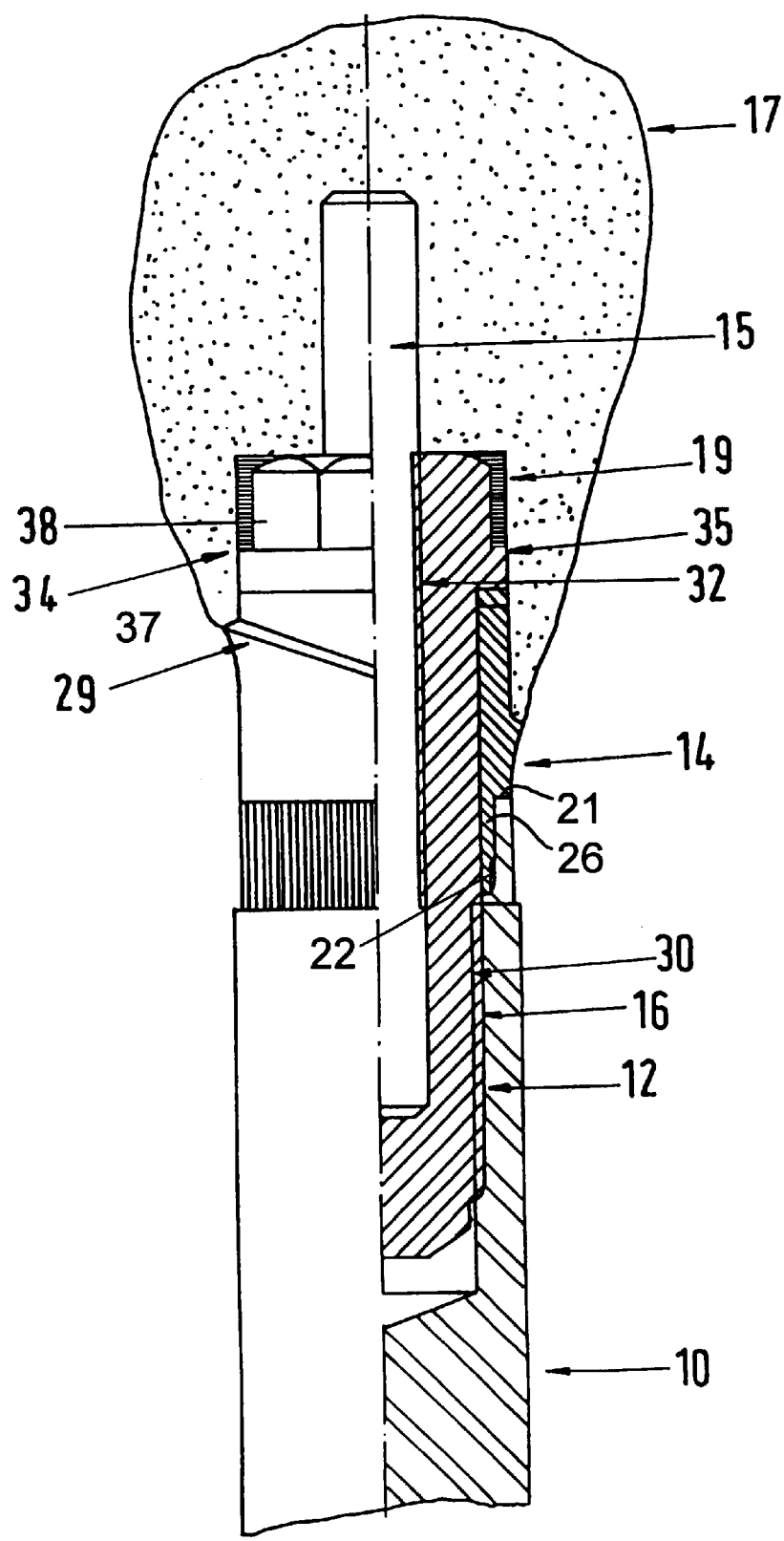
FIG. 1 is a partial longitudinal sectional view of an exemplary embodiment of the enossal single tooth implant of the invention in the assembled condition.

In the exemplary embodiment shown therein, the single tooth implant shown in FIG. 1 comprises a base member 10 of a known type as disclosed, for example, in German Letters Patent 38 39 724. The base member 10 in the illustrated embodiment is composed of titanium coated with titanium plasma. The single tooth implant further comprises a spacer sleeve means that is composed of a lower spacer sleeve part or member 12 and an upper spacer sleeve part 14. The outside circumference of the lower spacer sleeve part 12 is provided with a thread 30 that corresponds to the inside thread 16 of the base member 10. In its coronal region, the lower spacer sleeve part 12 comprises an inside thread 32 for a fastening tool in which an implant post 15 is cemented, as disclosed, for example, in German Letters Patent 39 17 690 or in German Letters Patent 38 39 724. A dental prosthesis in the form of a crown 17 that is cast with the implant post 15 is seated on the fastening head of the implant post 15.

Figure 2:
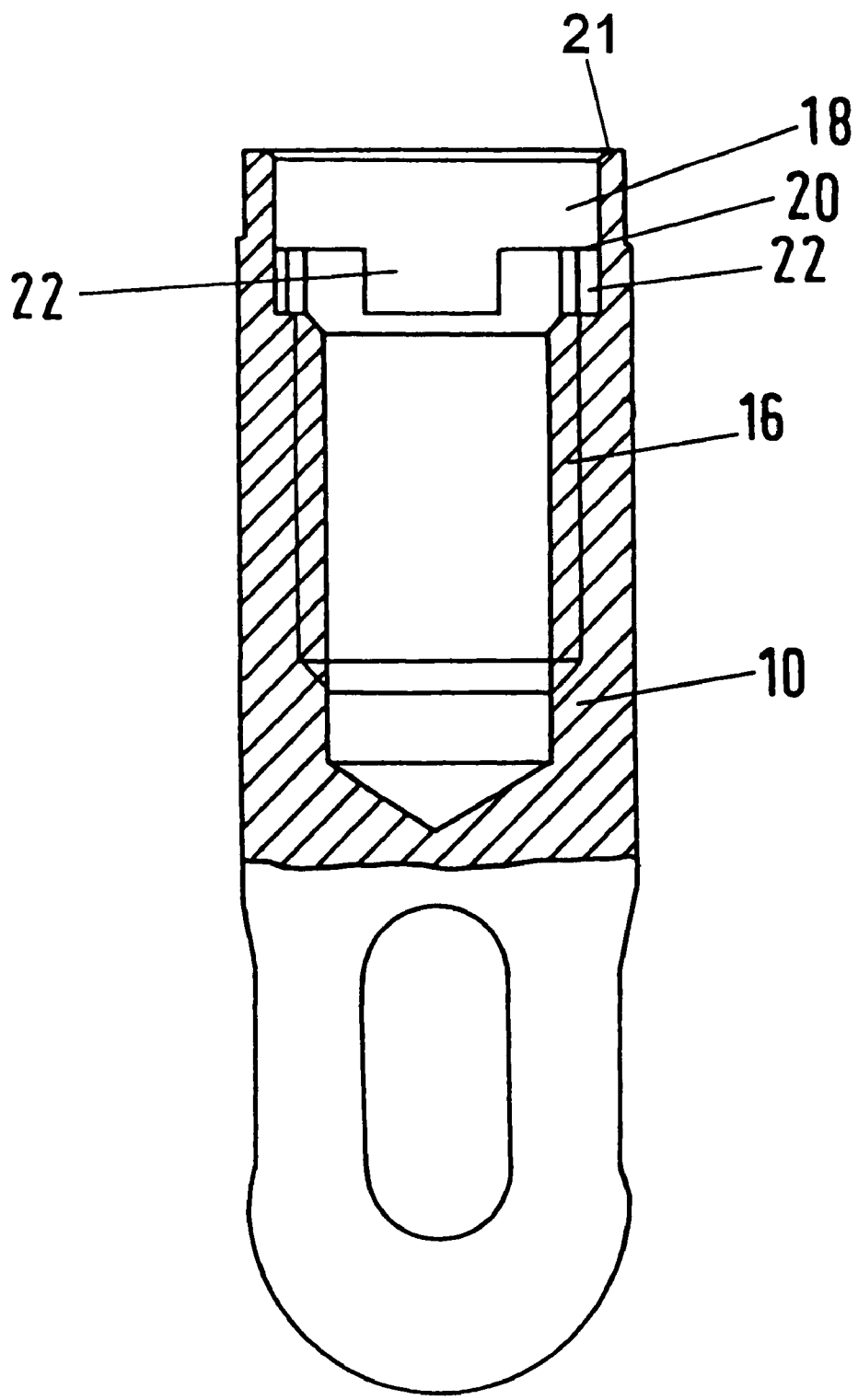
FIG. 2 is a longitudinal cross sectional view of the base member of the single tooth implant of FIG. 1.

FIG. 2 reveals that the base member 10 is provided with an inside thread 16 and comprises a ring recess 18 at what is the upper face edge 21 in the drawing. The inner or the cervical edge of the ring recess 18 adjoins a seating shoulder 20. Six positive lock pockets 22 which are arranged with uniform circumferential spacing are provided in the seating shoulder 20.

At an inner end or a cervical end which faces towards the bone (see FIG. 3), the upper spacer sleeve part 14 comprises a centering collar 24 whose outside diameter corresponds to the inside diameter of the ring recess 18 of the base member 10. The centering collar 24 comprises six positive lock tongues 26 arranged with uniform circumferential spacing that are complementary to the positive lock pockets 22 of the base member 10. The coronal part of the upper spacer sleeve part 14 exhibits a larger outside diameter than the centering collar 24 whereby a shoulder 28 is formed in the transition of the two parts or sections. At its circumference, the upper spacer sleeve part 14 comprises an all around joining shoulder 29 that, in adaptation to the anatomical conditions, has a peripherally varying spacing from the face edge of the base member.

In its coronal region, the lower spacer sleeve part 12 comprises a head section 34 (see FIG. 1) that provide an annular shoulder 35 whose outside diameter corresponds to the outside diameter of the larger outside diameter—in the coronal region—of the upper spacer sleeve part 14. The head section 34 merges into a cervical region whose outside diameter corresponds to the diameter of the inside bore of the base member.

A shoulder 38 for a tool in the form of a wrench is provided at the head section 34 end of the lower spacer sleeve part 12.

Figure 3:
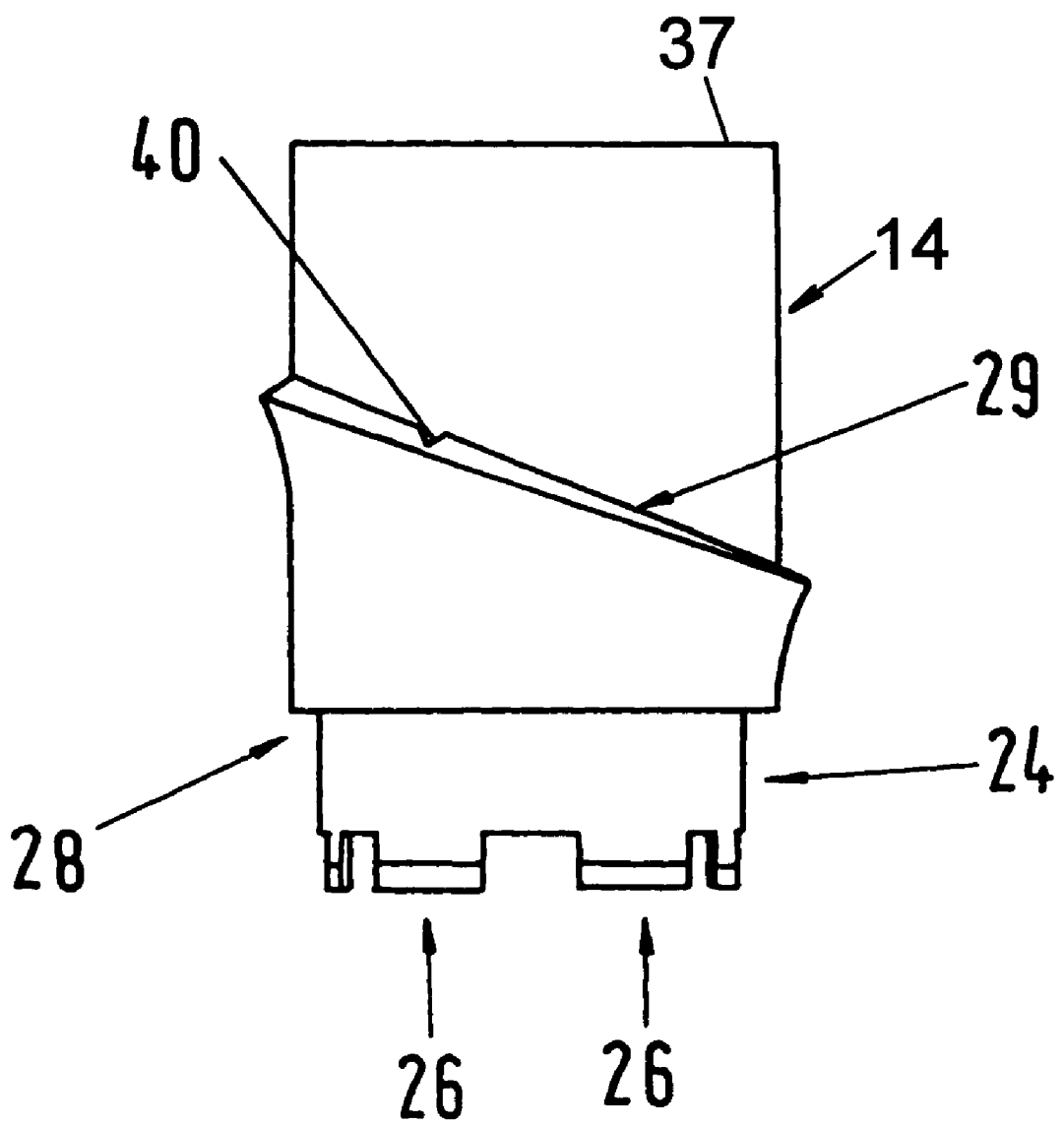
FIG. 3 is a side view of the upper spacer sleeve part of the single tooth implant of FIG. 1.

FIG. 3 reveals that the joining shoulder 29 is provided with a coronally directed adjustment notch 40 whose angular arrangement is defined relative to the positive lock elements 26. The adjustment notch 40 not only provides an improved possibility for applying a tool when fixing the spacer sleeve in the base member inserted into the jaw bone of the patient but, due to the angular definition of its position with respect to the positive lock elements 26, also yields the desired angular positioning of the joining shoulder 29 relative to the base member in that a suitable relative orientation of the spacer sleeve to the base member is selected from the relative orientations available as a result of the six positive lock elements.

The assembly of the described single tooth implant ensues as follows (see FIG. 1): the upper spacer sleeve part 14 is placed onto the base member 10 already held in the body tissue or, respectively, the jaw bone, whereby the positive lock tongues, interacting with the positive lock pockets 22, effect a plug-type connection secured against twisting. Subsequently, the lower spacer sleeve part 12 is threaded into the base member 10, whereby the shoulder 28 of the upper spacer sleeve part 14 is pressed against the upper face edge 21 of the base member 10 and the annular shoulder 35 of the lower spacer sleeve part 12 is pressed against the coronal circumferential edge 37 of the upper spacer sleeve part 14, so that the base member 10, the upper spacer sleeve part 14 and the lower spacer sleeve part 12 are connected to one another in axial direction.

What is thereby achieved over all is that the upper spacer sleeve part 14 has an annular shoulder 35 fixed relative to the base member 10 both in axial direction as well as in rotational direction. The implant post 15, which will be connected to the crown 17—the crown 17 has preferably been cast with the implant post 15—for constructing the dental prosthesis, is then cemented or threaded into the inside thread 32 of the lower spacer sleeve part 12. Subsequently, the dental prosthesis in the form of the crown 17 can be pushed onto the implant post 15 and fastened with a previously applied cement 19. The joining shoulder 29 thereby facilitates the attachment of the crown 17 and enables a matching of the shape and arrangement of the crown 17 to the anatomical conditions of the patient.

By meaningful employment of the adjustment notch 40, the angular orientation of the upper spacer sleeve part 14 relative to the base member 10 or, respectively, the lower spacer sleeve part 12 can be defined in a desired way, as already described above.

The bipartite spacer sleeve 12, 14 can be manufactured in various versions both in the height of the joining shoulder as well as in the base height (upper implant edge).

Both individually as well as in arbitrary combinations, the features of the invention disclosed above, in the drawing as well as in the claims can be critical for realizing the various embodiments of the invention.

We claim:

1. Enossal single tooth implant for a fixed dental prosthesis, comprising an essentially cylindrical base member insertable into a bore introduced into a jaw bone, said base member comprising a blind bore open toward one end to provide a coronal face edge, spacer sleeve means being attached in anti-twist fashion to the face edge of the base member, an implant post directly or indirectly introducible into the blind bore of the base member and at least partially penetrating the spacer sleeve means, and said implant having a fastening head for the dental prosthesis, the improvement comprising the spacer sleeve means having a first sleeve part with a circumferential surface forming part of the fastening head, said surface having an annular joining shoulder for the dental prosthesis lying in a plane being tilted to a plane extending perpendicular to a longitudinal axis of the implant and said joining shoulder having at least one coronally directed adjustment means so that the shoulder has a peripherally varying spacing from the coronal face edge of the base member for adaptation to any anatomical conditions.

2. Enossal single tooth implant according to claim 1, wherein the peripheral arrangement of the adjustment means is defined in terms of a circumferential angle with respect to the spacer sleeve part.

3. Enossal single tooth implant according to claim 1 wherein the implant post is connectable to the base member and secured against twisting.

4. Enossal single tooth implant according to claim 1 wherein a coronal region of the implant post at least partially serves as the fastening head for the dental prosthesis.

5. Enossal single tooth implant according to claim 1, wherein the spacer sleeve means includes a lower sleeve part which is fashioned with a closed end and is insertable into the open, one end of the base member and the lower sleeve part has a bore open toward a coronal end with an inside thread for securing the implant post.

6. Enossal single tooth implant according to claim 5, wherein the first sleeve part has a centering collar corresponding to the coronal face edge of the base member.

7. Enossal single tooth implant according to claim 6, wherein, the one end of the base member comprises a cylindrical ring recess for the acceptance of the centering collar of the first sleeve part.

8. Enossal single tooth implant according to claim 7, wherein the first sleeve part is provided with a second shoulder emplaceable onto the coronal face edge of the base member.

9. Enossal single tooth implant according to claim 8, wherein a coronal region of the first sleeve part comprises a longitudinal section with a larger outside diameter than a second region which forms the centering collar with an outside diameter that corresponds to the inside diameter of the cylindrical ring recess of the base member, wherein the second shoulder is formed in the transition of the two regions of different diameters, and a second coronal region of the lower sleeve part comprises a head section that forms an annular shoulder, whose outside diameter corresponds to the outside diameter in the first coronal region of the first sleeve part, and the second coronal region merges into a cervical region whose outside diameter corresponds to the diameter of the inside bore of the base member.

10. Enossal single tooth implant according to claim 9, wherein the second coronal region of the lower sleeve part has surfaces for engagement by a tool.

11. Enossal single tooth implant according to claim 6, wherein a connecting means for an anti-twist fastening of the spacer sleeve means on the base member is formed by a cylindrical ring recess of the base member having at least one base member positive lock element and the centering collar of the first sleeve part having at least one spacer sleeve positive lock element complementary to the base member positive lock element.

12. Enossal single tooth implant according to claim 11, wherein each base member positive lock element comprises an axial base member positive lock pocket in the seating shoulder of the ring recess, and the spacer sleeve positive lock element correspondingly comprises a complementary spacer sleeve positive lock tongue.

13. Enossal single tooth implant according to claim 12, wherein six positive lock elements arranged with uniform circumferential spacing are provided at the base member (10) and at the first sleeve part.

14. Enossal single tooth implant according to claim 11, wherein each base member positive lock element comprises a positive lock tongue extending from the seating shoulder of the ring recess and each spacer sleeve positive lock element comprises a complementary positive lock pocket in the collar.

15. Enossal single tooth implant according to claim 1, wherein the adjustment means comprises at least one notch formed in the shoulder.

* * * * *